United States Patent [19]

Schostarez

[11] Patent Number: 5,373,012
[45] Date of Patent: Dec. 13, 1994

[54] 5-FLUORO-2,4,6-PYRIMIDINETRIAMINE COMPOUNDS

[75] Inventor: Heinrich J. Schostarez, Portage, Mich.

[73] Assignee: The Upjohn Company, Kalamazoo, Mich.

[21] Appl. No.: 59,552

[22] Filed: May 10, 1993

Related U.S. Application Data

[63] Continuation-in-part of Ser. No. 612,695, Nov. 14, 1990, abandoned.

[51] Int. Cl.$^5$ .................. A61K 31/505; A61K 31/535; C07D 403/04
[52] U.S. Cl. .................................... 514/275; 544/320; 544/322; 544/323; 544/324; 544/326; 514/256
[58] Field of Search ............... 544/320, 322, 323, 324, 544/326; 514/275, 256

[56] References Cited

U.S. PATENT DOCUMENTS

| | | | |
|---|---|---|---|
| 3,382,247 | 5/1968 | Anthony et al. | 544/321 |
| 3,461,461 | 8/1969 | Anthony et al. | 424/45 |
| 3,464,987 | 9/1969 | Ursprung et al. | 544/123 |
| 3,644,364 | 2/1972 | Anthony | 544/323 |
| 4,139,619 | 2/1979 | Chidsey, III | 424/45 |
| 4,287,338 | 9/1981 | McCall | 544/123 |
| 4,596,812 | 6/1986 | Chidsey et al. | 514/256 |
| 4,885,296 | 12/1989 | Manouvy et al. | 514/252 |

OTHER PUBLICATIONS

Chemical Abstract, 70:115172v, pp. 353–354 (1969).
Chemical Abstract, 92:128848z, p. 696 (1980).
Advanced Organic Chemistry, 3rd ed., Jerry March, John Wiley & Sons Inc., pp. 602–603 (1985).

Primary Examiner—Mukund J. Shah
Assistant Examiner—Matthew V. Grumbling
Attorney, Agent, or Firm—Donald L. Corneglio

[57] ABSTRACT

A 5-fluoro-minoxidil compound and compositions are disclosed which are useful in the treatment of hair growth and cardiovascular disorders. The 5-fluoro-minoxidil compounds have been shown to have increased transdermal transport than minoxidil and therefore can be used in decreased amounts to achieve the same pharmacological efficacy of minoxidil.

3 Claims, 2 Drawing Sheets

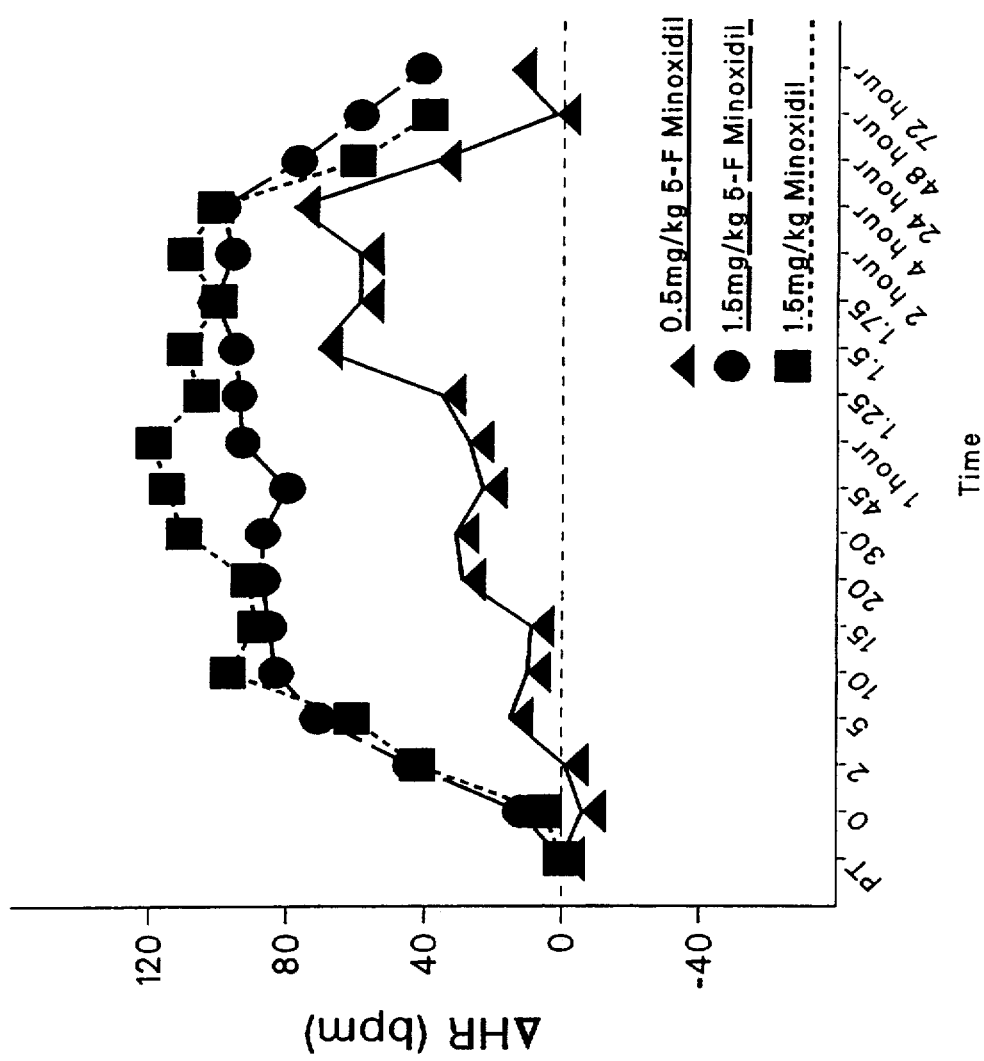

5-FLUORO-2,4,6-PYRIMIDINETRIAMINE COMPOUNDS

CROSS-REFERENCE TO RELATED APPLICATIONS

This application is a continuation of PCT/US 91/06728 (WO 92/08705), filed Sep. 20, 1991, which was a continuation-in-part of U.S. application Ser. No. 07/612,695, filed Nov. 14, 1990, abandoned.

BACKGROUND OF THE INVENTION

The present invention is directed toward a novel set of compounds, 5-fluoro-2,4,6-pyrimidinetriamines of Formula I or pharmaceutically acceptable salts thereof (hereinafter referred to as "5-fluoro minoxidil"), which are useful for the treatment of cardiovascular disorders and the promotion of hair growth. The use of minoxidil to treat cardiovascular disorders such as hypertension, congestive hear failure, and angina, peripheral vascular disorders and more recently to promote hair growth was recognized in the past and was extensively patented. Earlier patents to the minoxidil formulae itself are U.S. Pat. Nos. 3,461,461, 3,464,987 and 3,644,364 however they do not disclose or suggest a fluorine substitution even though bromine and chlorine were specifically named and in some cases iodide. Minoxidil for hair growth has also been patented in U.S. Pat. Nos. 4,139,619 and 4,596,812 however the minoxidil formulae claimed and disclosed in those patents did not show a 5-fluoro substituted minoxidil.

One explanation for this apparent deletion from the halogen family was that the fluorine atom was difficult to substitute onto the pyrimidine ring at this particular position.

The subject invention provides a method for substituting fluorine at the 5-position on a minoxidil compound and shows that this particular species has significant advantages over its halogen analogs. The 5-fluoro substituted minoxidil has bene found to have superior transdermal transport properties over unsubstituted minoxidil. The increased amount of minoxidil that is transported into the epidermis means that less can be topically applied to achieve the same hair growth pharmacological efficacy as compared to other non-fluoride substituted minoxidils. Also, because less active ingredient is used, there is significantly reduced side effects when the compound is used for hair growth.

INFORMATION DISCLOSURE

U.S. Pat. No. 4,885,296 discloses methods of preparation and compounds of 1-piperazinylpyrimidine similar to Formula I (X is O) but without the fluorine substitution.

U.S. Pat. No. 4,287,338 discloses methods of preparation and compounds of sulfooxy-pyrimidinium, -pyridinium and -triazinium similar to Formula I (X is $OSO_2O$) but without a fluorine substitution.

U.S. Pat. No. 3,644,364 discloses methods of preparation and compounds of 6-substituted-4-amino-1,2-dihydro-1-hydroxy-2-iminopyrimidines similar to Formula I (X is OH) but without the fluorine substitution. U.S. Pat. No. 3,464,987 discloses similar compounds with a lower alkyl substitution at the 6-position but does not disclose a fluorine substitution.

U.S. Pat. No. 3,461,461 discloses methods of preparation and compounds of 1,2-dihydro-1-hydroxypyrimidines similar to Formula I (X is OH) but without fluorine substitution.

U.S. Pat. No. 3,382,247 discloses methods of preparation and compounds of 6-amino-1,2-dihydro-1-hydroxy-2-imino-4-phenoxypyrimidines similar to Formula I (X is OH) but without a fluorine substitution.

Methods and other minoxidil compositions and compounds used for the stimulation of hair growth are disclosed in U.S. Pat. Nos. 4,139,619 (topical composition for treating alopecia) and 4,596,812 (methods for treating alopecia).

SUMMARY OF THE INVENTION

In one aspect, the present invention involves the use of a 5-fluoro minoxidil composition, Formula I, for the promotion of hair growth in mammals, especially humans. Promotion of hair growth is where the growth of hair is induced or stimulated or where the loss of hair is decreased. More specifically, any of the various analogs of the 5-fluoro minoxidil can be used for the treatment of human alopecia, including alopecia areata, androgenetic alopecia and other hair growth disorders.

The method comprises the application of an effective amount of Formula I to promote hair growth. Typically, amounts from about 0.01 to about 20, 0.1 to 10, preferably, 0.5 to 5, more preferably 1to 3 percent by weight of a compound of Formula I are applied.

The method can also comprise the application of an effective amount of such compounds admixed in a pharmaceutical carrier adapted for topical application. In another aspect the method includes the routine application of such compound to an area of treatment. Further the routine application can comprise a plurality of treatments such as, for example, daily or twice daily to promote hair growth.

In another aspect, the present invention involves the use of a 5-fluoro minoxidil composition, Formula I, for the treatment of cardiovascular disorders by parenteral, oral or transdermal administration.

BRIEF DESCRIPTION OF THE DRAWINGS

FIG. 2 is a chart showing changes in heart rate versus time at the doses indicated for 5-fluoro minoxidil and minoxidil.

DETAILED DESCRIPTION OF THE INVENTION

Figure 1:
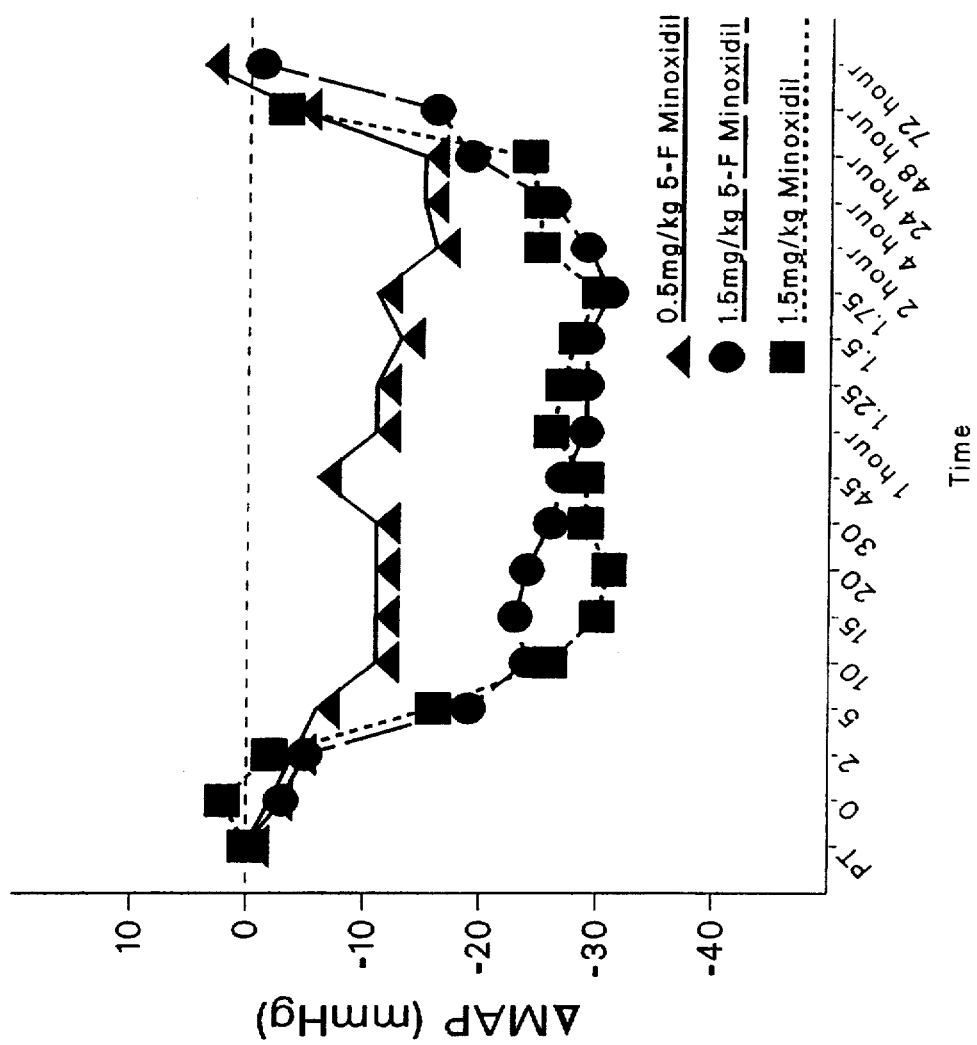
FIG. 1 is a chart showing changes in mean arterial pressure versus time at the doses indicated for 5-fluoro minoxidil and minoxidil.

The present invention is directed toward novel 5-fluoro-2,4,6-pyrimidinetriamine, 1-oxide derivatives as shown in Formula I (5-fluoro minoxidil):

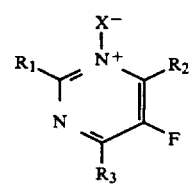

wherein X is O or $OSO_3$; $R_1$ is $NH_2$, NH—($C_1$–$C_5$ alkyl), and NH—CO—$R_4$; $R_2$ is NH$_2$, CH$_3$, CF$_3$, NH—CO—$R_4$; $R_3$ is —N($R_5$)($R_6$) wherein $R_5$ and $R_6$ are independently selected from the group consisting of hydrogen with the proviso that both are not simultaneously hydrogen. $C_1$-$C_8$ alkyl, $C_2$-$C_{10}$ alkenyl, arylalkyl, and $C_3$-$C_{10}$ cycloalkyl and the heterocyclic moieties, aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties may have attached as substituents on their carbon atoms, zero to 3 $C_1$-$C_5$ alkyls, inclusive, a nitrogen atom of each of said heterocyclic moieties being the point of attachment of $R_3$ to the ring in said formula; and $R_4$ is O—($C_1$-$C_6$ alkyl), CO—O—($C_1$-$C_6$) alkyl. It is understood that $C_1$-$C_6$ alkyl includes branches and cyclic derivatives.

An "alkyl" is a straight or branched carbon chain containing the number of carbon atoms designated. An "alkenyl" is a straight or branded carbon chain having three to ten carbon atoms and containing at least one degree of unsaturation.

An "arylalkyl" is a benzyl, phenylethyl, 1-phenylethyl, 2-phenylpropyl, 4-phenylbutyl, 6-phenylhexyl, 5-phenyl-2-methylpentyl, 1-naphthylmethyl, 2-(1-napthyl)ethyl, 2-(2-napthyl)ethyl, and the like.

A "cycloalkyl" is a cyclic ring structure formed three to ten carbon atoms. The cyclic structure may also contain an alkyl substitution wherein the total carbons are calculated to include this substitution.

"Pharmacologically acceptable salts" are acid addition salts which can be prepared by any of the art recognized means. Typical, acid addition slats include hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates, fumarates and other pharmaceutically acceptable counter ions for amines.

This novel series of 5- fluorinated minoxidil analogues are useful in the treatment of cardiovascular disorders, such as hypertension, congestive heart failure, and angina, peripheral vascular disorders, and the treatment of alopecia, various forms such as alopecia areata, alopecia totalis, alopecia universalis and androgenetic alopecia. The subject compounds exhibit potent hypotensive activity in the dog and has exhibited activity in a in vivo hair growth rat assay. Since the subject compounds are hypotensive agents which can induce vasodilation, they can be useful as a treatment for male erectile dysfunction. Preferably the compounds are applied topically at the glans penis.

The invention also relates to compounds as described in Formula I, and combinations with antiinflammatories (steroidal and non-steroidal), androgen receptor blockers, 5α-reductase inhibitors, and β-blockers for the treatment of cardiovascular disorders, such as hypertension, congestive heart failure, and angina, peripheral vascular disorders, and the treatment of alopecia, various forms such as alopecia areata, alopecia totalis, alopecia universalis and androgenetic alopecia.

A synthesis scheme for the subject compounds is depicted on Scheme Sheet 1, below and is explained as follows:

Commercially available dimethyl fluoromalonate (1) (or the diethyl ester) is condensed with guanidine hydrochloride (2) to yield 4,6-dihydroxy-5-fluoro-2-pyrimidineamine (3). This product (3) was converted to the dichloride (4) with $POCl_3$/2-picoline. Introduction of the 4-amino group was carried out undersealed tube conditions to give (5). Oxidation of (5) with MCPBA formed the N-oxide (6) which was smoothly converted to the 5-fluoro minoxidil with piperidine in refluxing ethanol.

The compounds of the subject invention can be used for hair growth which comprises the treatment of the skin with an effective amount of Formula I, including its pharmaceutically acceptable salts whereby hair growth is promoted. The method and composition of this invention are useful for increasing hair growth over that normally experienced by the treated subject, maintaining hair growth where hair growth was previously declining or obtaining hair growth were hair growth has stopped.

Pharmaceutically acceptable salts of Formula I, are for example acid addition salts may be chosen from the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

Typically, in a hair growth application a compound of formula I is applied to the skin region where the promotion of hair growth is desired with a pharmaceutical carrier. "Promotion of hair growth" is meant to include the increase of hair growth over normal hair growth or the initiation of hair growth where hair growth has stopped prior to treatment with Formula I. More preferably, the pharmaceutical carrier is adapted for topical application such as those pharmaceutical forms which can be applied externally by direct contact with the surface to be treated.

Conventional pharmaceutical carriers or vehicles for this purpose include ointments, waxes, lotions, pastes, jellies, sprays, aerosols, and the like in aqueous or nonaqueous formulations. The term "ointment" embraces formulations (including creams) having oleaginous, absorption, water-soluble and emulsion-type bases, e.g., petrolatum, lanolin, propylene glycol, propylene carbonate, polyethylene glycols, N-methyl pyrrolidinone, oleyl alcohol, ethyl alcohol as well as mixtures of these. The use of penetration enhancers such as oleyl alcohol in concentrations of about 1% by weight may be beneficial. For example, as mixture of 84% propylene carbonate, 15% N-methylpyrrolidinone and 1% oleyl alcohol may be an effective vehicle for a hair growth promoter.

Preparation of minoxidil topical compositions are disclosed in U.S. Pat. Nos. 4,139,619 and 4,596,812, both herein incorporated by reference for their disclosure of the preparation of topical carriers as well as the preparation of a minoxidil topical preparation to which Formula I can be admixed.

Additionally, the 5-fluoro minoxidil compounds can be admixed with other compounds for the treatment of hair growth. Such compounds which can be included in the overall composition or treatment are minoxidil, pyranobenzoxadiazole, vasoconstrictors such as betamethasone dipropionate, corticosteroids such as hydrocortisone, triazines, scopolamine, antiandrogens such as cyproterone acetate, cyoctol and 5-α-reductase inhibitors such has 17β-(N-tert-butylcarbamoyl)-4-aza-5-α-androst-1-en-3-one.

Any of the above additional compounds or mixtures thereof can be admixed with a 5-fluoro minoxidil compounds to form a pharmaceutically effective hair growth composition. The 5-fluoro minoxidil compound is added in an effective amount which is an amount sufficient to promote hair growth. Typically, the compound is present in an amount of from about 0.01 to about 20, from about 0.1 to about 10, from about 0.5 to about 5, or more preferably 1 to about 3 percent by weight of the composition.

The compound of formulated composition can be applied to the area to be treated, such as the scalp in humans, by spraying, dabbing or swabbing. Other less specific methods can be employed provided the active ingredient, compound of Formula I or II, is delivered to the region of a hair follicle. Preferably, the compound or formulated composition is periodically applied to the treatment area on a routine basis prior to, during and subsequent to hair growth. Generally, the routine treatment would be to apply the compound or formulated composition at least daily, preferably twice daily although more frequency applications can be used. The treated area will experience over a period of time and applications increased or stimulated hair growth or a decrease in the loss of hair.

The percentage by weight of the compound of Formula I herein utilized ranges from about 0.01% to about 20% of the pharmaceutical preparation preferably from about 0.5 to about 5% or preferably from about 1 to about 3%. In these preparations the pharmaceutical carrier for topical applications constitutes a major amount of the preparation.

The 5-fluoro minoxidil compounds were evaluated for hair growth in an in vivo hair growth assay using rats. Each rat is dosed with vehicle and drug, 200–500 microliters per day, 5 days per week. Every seven days the treated areas are shaved and the hair removed is weighed to compare normal untreated hair growth to the drug treated hair growth. After treatment of several months, the subject compositions significantly improve the condition of the hair. The results of the biological evaluation are presented in Table I.

TABLE I

| Group | Hair Growth[1] | p vs Vehicle |
| --- | --- | --- |
| 1 mM | +0.609 ± 0.083 | 0.49 |
| 5 mM | +0.760 ± 0.153 | 0.19 |
| 25 mM | +0.952 ± 0.149 | 0.02 |
| Vehicle[2] | +0.527 ± 0.081 | — |

[1]Presented as mean mg/in$^2$/day.
[2]Vehicle 50/30/20: Propylene glycol/Ethanol/Water.

In Table II a direct comparison of minoxidil to a reduced amount of 5-fluoro-minoxidil was made—100 mM minoxidil to 25 mM 5-fluoro-minoxidil. This was to demonstrate the increased efficacy of the 5-fluoro-minoxidil which therefore allow a lower amount to be used to obtain similar results. The topical applied dose and vehicle was designed to provide comparable levels of transdermal delivery. The table II data shows that there is no statistical difference (p) observed when the level of hair growth stimulation of test two agents is compared.

TABLE II

| Compound | Hair Growth[3] | p |
| --- | --- | --- |
| Minoxidil & 100% PG[1] | +1.065 | 0.002 |
| 100% PG[1] | +0.487 | — |
| 5-Fluoro-minoxidil & Vehicle[2] | +0.938 | 0.023 |

TABLE II-continued

| Compound | Hair Growth[3] | p |
| --- | --- | --- |
| Vehicle[2] | +0.528 | — |

[1]PG is propylene glycol.
[2]Vehicle 50/30/20: Propylene glycol/Ethanol/Water.
[3]Presented as mean mg/in$^2$/day.

The 5-fluoro minoxidil compounds were evaluated in the macaque monkey models and show significant hair growth results.

Thirteen stumptail macaque (Macaca specoisa) monkeys (mixed sexes) were assigned to vehicle control and drug treated groups on the basis of baseline hair weight data.
1. Topical 50:50 vehicle (N=7)
2. Topical 100 mM U-83,868 (N=6)

The control consisted of 50% propylene glycol, 50% ethanol. The experimental composition consisted of a 100 mM concentration of topical 5-fluoro minoxidil formulated in the control vehicle. Immediately prior to the dosing phase of the study, hair was removed from a 1 inch square area (identified by four tattoos) in the center of the balding scalp. This hair collection was the baseline hair growth determination prior to the beginning of treatment. Approximately 250 μL of vehicle or 100 mM 5-fluoro minoxidil (prepared in vehicle)were topically administered to the tattooed area of the scalp. The monkeys were dosed once per day, five days per week for sixteen weeks.

At four week intervals throughout the dosing phase of the study, each monkey was shaved and the hair was collected and weighed. The body weight data (at baseline and during assay) were analyzed by the nonparametric Wilcoxon rank-sum test. Differences were significant at p<0.05. The hair weight data (mean±SEM) at each 4 week collection for vehicle and treatment groups were expressed as the change from baseline. Statistical analysis (ANOVA) was performed on the ranks of the data to show overall differences among groups at each 4 week collection with p<0.10 marginally significant, p<0.05 significant, and p<0.01 highly significant. The results after sixteen weeks of dosing is shown in Table III.

TABLE III

| Group | Hair Growth (mg)[1] | p vs Vehicle |
| --- | --- | --- |
| 5-fluoro minoxidil | +14.8 ± 3.1 | <0.01 |
| Vehicle | −1.8 ± 2.7 | — |

[1]Cumulative change in hair weight from baseline.

The above data shows a statistically significant increase in the promotion of hair growth which represents a significant advancement in the art of promoting, maintaining, or restoring hair growth.

The 5-fluoro minoxidil compounds were evaluated for cardiovascular effects in an in vivo test with beagle dogs. This test procedure is described in Humprey SJ, Zins GR, Whole Body and Regional Hemodynamic Effects of Minoxidil in the Conscious Dog, J. Card, Pharm. 6:979-88 (1984) and in Humprey, S.J., Zins, G.R., The Effects of Indomethacin on the Systemic and Regional Vasodilator Responses to Minoxidil in the Conscious Dog, Chem. Path. & Pharm. 59:1 3–20 (1988). Experiments were conducted using a radiolabeled tracer microspheres technique, Wagner NH et al., Studies of the Circulation with Radioactive Microspheres, Invest. Radiol. 4:374–86 (1969), with conscious beagle dogs.

The results of a rapid evaluation (N=1) of the 5-fluoro minoxidil compound compared to minoxidil are presented in FIG. 1 change in Mean Arterial Pressure versus Time at the doses indicated and FIG. 2 Changes in Heart Rate versus Time at the doses indicated. At equivalent doses (1.5 mg/kg) both compounds, the 5-fluoro minoxidil and minoxidil, produce similar decreases in MAP (Mean Arterial Pressure) as well as increases in heart rate. The fluorinated analogue is at a minimum equivalent to minoxidil in this model.

The Formula I compounds are used for the treatment of cardiovascular disorders wherever a potent hypotensive drug is indicated. The compounds and compositions of Formula I are administered in a therapeutic effective amount which is an amount sufficient to control hypertension, congestive heart failure, angina and peripheral vascular disorders in the host being treated such as mammals which includes humans. Typically, the Formula I compounds are used in unit dosages of from 0.01 to 300 mg in oral or injectable preparations. Preferably, the Formula I compounds are used in unit dosages of 0.001 to 10 mg/kg for administration by routes either oral, sublingual, transdermal, or parenteral such as by subcutaneous, intramuscular, or intravenous injection.

The particular dose of compound administered according to this invention will of course be determined by the particular circumstances surrounding the case, including the compound administered, the route of administration, the particular cardiovascular disorder being treated, and similar considerations.

The Formula I compounds can be formulated into typical pharmaceutical preparations for either oral or parenteral administration. For example, the Formula I compound can be formulated into a composition by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelation capsules for convenient oral administration.

A gelatin capsule suited to oral administration may contain, for example, a Formula I compound in the amount of about 0.1 to about 100 mg. Such formulation can be administered orally as often as needed depending upon the particular condition and patient being treated.

For parenteral administration a Formula I compound can be formulated for intramuscular or intravenous administration. In the case of treatment of a patient suffering from a severe cardiac arrhythmia, it may be desirable to administer the Formula I compound by intravenous infusion in order to effect a speedy conversion to a normal cardiac rhythm. Such normal condition can then be maintained by oral administration.

The compositions of the present invention may also include sustained release oral dosage forms and controlled release dosage forms by which the effect of the dosage is through the skin. Such compositions are those known to an ordinary skilled artisan or can be ascertained by ordinary experimentation from known compositions such as creams, gels, pastes or liquids. Typical transdermal compounds are polyethylene glycol, triacetin, propylene glycol, propylcarbonate, ethanol, water, isopropyl myristate and various mixtures thereof.

The ability of the 5-fluoro minoxidil to be absorbed in transdermal applications was measured versus minoxidil as a control. Three rats were treated with each compound for four days and on the fifth day their urine was collected over a 24 hour period. The urine was then analyzed for drug levels and converted to micrograms urine excreted per 24 hours. The compounds were administered in a 50/30/20 propylene glycol/ethanol/water vehicle. The results shown in Table IV were as follows:

TABLE IV

| COMPOUND | TOTAL MICROGRAMS EXCRETED | AVERAGE |
| --- | --- | --- |
| Minoxidil (Control) | | |
| 1 | 354 | 454 |
| 2 | 358 | |
| 3 | 651 | |
| 5-Fluoro Minoxidil | | |
| 1 | 1229 | 1427 |
| 2 | 1132 | |
| 3 | 1921 | |

The results indicate that 5-fluoro minoxidil has superior absorption over the minoxidil control.

In the following preparation of 5-fluoro minoxidil, high resolution mass spectra, infrared spectra, ultraviolet spectra, and combustion analyses were obtained on the subject compounds. High field $^1$H-NMR spectra at 300 Mhz and $^{13}$C spectra at 75 Mhz were determined on a Bruker AM-300 and chemical shifts reported as δ units relative to tetramethylsilane.

Thin-layer chromatography was conducted with Analtech 0.25 mm glass plates precoated with silica gel GF. For column chromatography. E. Merck silica gel 60, 230–400 mesh, or E. Merck prepacked Lobar columns were used. All solvents for chromatography were Burdick and Jackson or Fisher reagent grade. All non-aqueous reactions were carried out under an inert argon atmosphere unless otherwise noted.

EXAMPLE 1:
5-Fluoro-6-piperidinyl-2,4-pyrimidinediamine

A. Preparation of
5-Fluoro-4,6-dihydroxy-2-pyrimidineamine (3)

Sodium (257 mg, 11 mmol) was dissolved in absolute ethanol (50 ml) with stirring under argon. When the sodium had thoroughly dissolved, guanidine hydrochloride (2) (502 mg, 5 mmol) and diethyl fluoromalonate (1) (790 mg, 4.4 mmol) were added. The solution was left to stir at room temperature overnight. A condenser was then attached to the flask and the solution was refluxed under argon for 4.5 hours. The solution was cooled to room temperature and concentrated. The residue was redissolved in 20 ml hot $H_2O$ and acidified to pH 4. The mixture was cooled on ice and the precipitate was collected, yielding (3) as a peach colored solid (618 mg, 96%): MS (70 eV, EI)m/z (relative intensity) 146(M+, 100), 18 (95), 172 (26), 17 (24), 300 (21); IR (mull, cm$_{-1}$) 3363, 1695, 1601, 1420, 1208, 677, 666; UV (MeOH, nm) 206(3,840), 235(3,380), 270(11,600). Exact Mass Calcd for $C_4H_4N_3O_2F$: 146.0366. Found: 146.0371.

B. Preparation of
5-fluoro-4,6-dichloro-2-pyrimidineamine (4)

5-Fluoro-4,6-dihydroxy-2-pyrimidineamine (3) (450 mg, 3 mmol), phosphorous oxychloride (972 mg, 6 mmol) and 2-picoline (633 mg, 7 mmol) were charged to a 15 ml round bottom flask and heated at 110° C. for 3.5 hours. The reaction mixture was then poured onto ice. The ice solution was neutralized to pH 5.5 and refluxed under argon for 1 hour. The solution was cooled on ice and the precipitate was collected, yielding (4) as a brown solid (268 mg, 47%): MS (70 eV, EI) m/z (relative intensity) 101 (M+, 181) 183 (66), 146 (56), 85 (34), 154 (28). Exact Mass Calcd for C₄H₂N₃Cl₂F: 180.9610. Found: 180.9607.

C. Preparation of 5-Fluoro-6-chloro-2,4-pyrimidinediamine (5)

5-Fluoro-4,6-dichloro-2-pyrimidineamine (4) (204 mg, 1 mmol) and ammonium hydroxide (15 ml) were charged to a sealed tube and ethanol (1.5 ml) added. The tube was heated at 100° C. for 24 hours. The solution was concentrated. The residue was absorbed on silica gel and chromatographed (elution with ethyl acetate), yielding (5) as a white powder (118 mg, 65%): MS (70 eV, EI) m/z (relative intensity) 162 (M+, 100), 43 (92), 164 (33), 127 (29), 135 (16). Exact Mass Calcd for C₄H₄N₄ClF: 162.0108. Found: 162.0100.

D. Preparation of 5-Fluoro-6-chloro-2,4-pyrimidinediamine, 3-oxide (6)

3-Chloroperoxybenzoic acid (303 mg, 1.4 mmol) and methanol (6 ml) were charged to a round bottom flask, which was then evacuated, flushed with argon and cooled to 0° C. After cooling, (5) (115 mg, 0.7 mmol) was added to the solution with the air of additional cold methanol (6 ml). The solution was stirred at 0° C. under argon for 5 hours and then slowly warmed to room temperature overnight. The solution was concentrated. The residue was absorbed on silica gel and chromatographed (elution with 20% methanol/chloroform+3% ammonium hydroxide), yielding (6) as a white solid (63 mg, 50%): MS (70 eV, EI)m/z (relative intensity) 178 (M+, 100), 43 (60), 180 (33), 85 (28), 44 (18). Exact Mass Calcd for C₄H₄N₄OF: 178.0058. Found :178.0060.

E. Preparation of 5-Fluoro-6-piperidinyl-2,4-pyrimidinediamine, 3-Oxide

5-Fluoro-6-chloro-2,4-pyrimidinediamine, 3-oxide (6) (58 mg, 0.32 mmol), piperidine (112 mg, 1.3 mmol) and 95% ethanol (2.6 ml) were charged to a round bottom flask and refluxed for 2 days. The solution was concentrated and the residue was chromatographed on silica gel (elution with 15% methanol/chloroform+2% ammonium hydroxide), yielding 5fluoro-6-piperidinyl-2,4-pyrimidinediamine 3-oxide as a white solid. (51 mg, 69%): MS (70 eV, EI)m/z (relative intensity) 84 (100), 227 (M+, 98), 210 (55), 43 (30), 40 (24); ¹H NMR (CD₃OD)δ4.91 (s, 4H), 3.61 (mult., 4H), 1.67 (mult., 2H), 1.60 (mult., 4H); ¹³C NMR (CD₃OD) ppm 150, 147.5, 147, 123, 49.86, 27.05, 25.82. Exact Mass Calcd for C₉H₁₄N₅OF: 227.1182. Found: 227.1188.

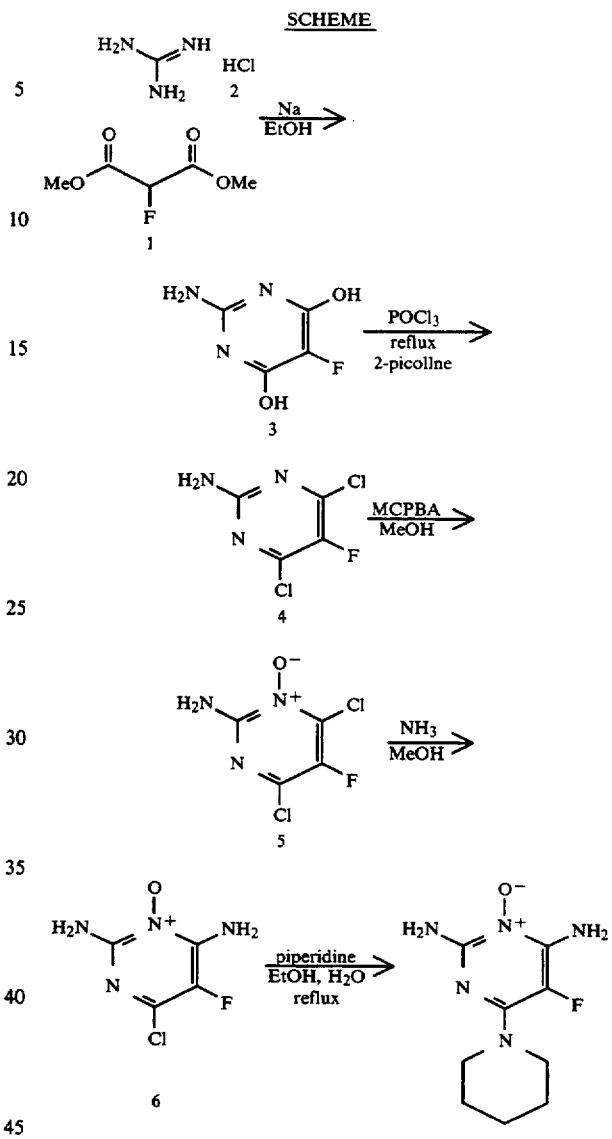

SCHEME

I claim:

1. A compound which is 5-fluoro-6-piperidinyl-2,4-pyrimidinediamine.

2. A method for treating cardiovascular disorders in a patient in need thereof comprising the administration of a therapeutically effective amount of 5-fluoro-6-piperidinyl-2,4-pyrimidinediamine.

3. A method for promoting hair growth in a patient in need thereof comprising the topical administration of a therapeutically effective amount of 5-fluoro-6-piperidinyl-2,4-pyrimidinediamine.

* * * * *